(12) United States Patent
Soma et al.

(10) Patent No.: US 11,529,229 B2
(45) Date of Patent: Dec. 20, 2022

(54) INTRAOCULAR LENS, INTRAOCULAR LENS FIXING ASSISTANCE SYSTEM, AND IMAGE PROCESSING APPARATUS

(71) Applicant: SONY CORPORATION, Tokyo (JP)

(72) Inventors: Yoshio Soma, Tokyo (JP); Tomoyuki Ootsuki, Tokyo (JP); Junichiro Enoki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/049,533

(22) PCT Filed: Mar. 22, 2019

(86) PCT No.: PCT/JP2019/011970
§ 371 (c)(1),
(2) Date: Oct. 21, 2020

(87) PCT Pub. No.: WO2019/216036
PCT Pub. Date: Nov. 14, 2019

(65) Prior Publication Data
US 2021/0259824 A1 Aug. 26, 2021

(30) Foreign Application Priority Data
May 8, 2018 (JP) .............................. JP2018-089794

(51) Int. Cl.
*A61F 2/16* (2006.01)
(52) U.S. Cl.
CPC ........ *A61F 2/16* (2013.01); *A61F 2002/1681* (2013.01); *A61F 2250/0097* (2013.01)

(58) Field of Classification Search
CPC ................ A61F 2/16; A61F 2250/0097; A61F 2002/1681; A61F 2250/0085
See application file for complete search history.

(56) References Cited

U.S. PATENT DOCUMENTS

2006/0235428 A1* 10/2006 Silvestrini ............... A61F 9/007
606/107
2011/0118836 A1* 5/2011 Jain .......................... A61F 2/16
623/6.43

(Continued)

FOREIGN PATENT DOCUMENTS

CA       2614543 A1    10/2006
CN      101198294 A     6/2008
(Continued)

OTHER PUBLICATIONS

International Search Report and Written Opinion of PCT Application No. PCT/JP2019/011970, dated May 14, 2019, 08 pages of ISRWO.

*Primary Examiner* — Javier G Blanco
(74) *Attorney, Agent, or Firm* — Chip Law Group

(57) ABSTRACT

To provide an intraocular lens to which a mark for assisting more accurate fixation in an eye has been applied. Provided is an intraocular lens including an optical part having a mark that is detectable under illumination of a specific wavelength range outside a wavelength range of visible light, and a support part that supports the optical part, in which the mark is indicated by a geometric pattern that allows for identification of an optical center position of the optical part and information regarding posture of the optical part in an eye.

9 Claims, 16 Drawing Sheets

(56) References Cited

U.S. PATENT DOCUMENTS

2011/0264209 A1* 10/2011 Wiechmann .......... A61F 2/1613
                                                            623/6.6
2013/0073039 A1*  3/2013 Mirlay ................. A61F 2/1632
                                                            623/6.38

FOREIGN PATENT DOCUMENTS

| DE | 102008017592 A | 10/2009 |
|----|----------------|---------|
| JP | 2008-536576 A  | 9/2008  |
| JP | 2011-516134 A  | 5/2011  |
| JP | 2011-245208 A  | 12/2011 |
| WO | 2006/113411 A1 | 10/2006 |
| WO | 2009/124838 A2 | 10/2009 |

* cited by examiner

INTRAOCULAR LENS, INTRAOCULAR LENS FIXING ASSISTANCE SYSTEM, AND IMAGE PROCESSING APPARATUS

CROSS REFERENCE TO RELATED APPLICATIONS

This application is a U.S. National Phase of International Patent Application No. PCT/JP2019/011970 filed on Mar. 22, 2019, which claims priority benefit of Japanese Patent Application No. JP 2018-089794 filed in the Japan Patent Office on May 8, 2018. Each of the above-referenced applications is hereby incorporated herein by reference in its entirety.

TECHNICAL FIELD

The present disclosure relates to an intraocular lens, an intraocular lens fixing assistance system, and an image processing apparatus.

BACKGROUND ART

As a method for refractive correction in ophthalmology, inserting an artificial lens called an intraocular lens (IOL) into an eye to eliminate a lens refractive error and improve visual functions such as visual acuity is widely used. The most widely used intraocular lens is an intraocular lens that is inserted into a lens capsule as a substitute for the lens removed by cataract surgery. There is a variety of intraocular lenses such as an intraocular lens (phakic IOL) placed or fixed (hereinafter, these may be collectively referred to simply as "fixed") in, for example, a ciliary sulcus besides the lens capsule.

In any type of intraocular lens, in order to maximize an effect of refractive correction obtained, it is important to select a lens with an appropriate power or shape based on a preoperative examination and fix the lens in a correct position in the eye. For this reason, a method of assisting a work for fixing an intraocular lens in a correct position and posture in an eye has conventionally been proposed.

For example, in a case of a toric intraocular lens that corrects astigmatism, a toric axis of the intraocular lens (axis perpendicular to an XY plane) needs to be aligned with an astigmatic axis of a patient (axis perpendicular to an XY plane), and a sufficient astigmatism correction effect cannot be obtained in a case where there is a displacement in orientation (rotation about a Z axis). Thus, the toric intraocular lens has a mark indicating the toric axis at an end point so that the orientation of the intraocular lens can be grasped. For example, Patent Document 1 discloses a toric intraocular lens in which a visible mark indicating a direction of an astigmatic axis is formed on an optical part of the intraocular lens. When the toric intraocular lens is inserted, it is possible to adjust the orientation of the lens while viewing the mark so that the toric intraocular lens is fixed with accurate orientation.

CITATION LIST

Patent Document

Patent Document 1: Japanese Patent Application Laid-Open No. 2011-245208

SUMMARY OF THE INVENTION

Problems to be Solved by the Invention

As the mark indicating the astigmatic axis of the toric intraocular lens described in Patent Document 1 described above is provided near an outer edge of the optical part, a mark applied to an intraocular lens is provided near an outer edge of an optical part. This is because in a case where a mark is provided in a visible state on the optical part, the mark obstructs a field of view of a wearer of the intraocular lens. However, at a time of fixing a toric intraocular lens in an eye, in a case where a mark is applied at an optical center position of an optical part, the intraocular lens can be fixed more easily and accurately.

Furthermore, as described in Patent Document 1 described above, a mark of a conventional intraocular lens can indicate only the orientation of the intraocular lens. However, if, besides information indicating the astigmatic axis, information indicating, for example, the center position or tilt of the intraocular lens can also be obtained from the mark of the intraocular lens, the intraocular lens can be more accurately fixed in the eye.

Thus, the present disclosure proposes new and improved intraocular lens, intraocular lens fixing assistance system, and image processing apparatus, in which a mark for assisting more accurate fixation in an eye is applied.

Solutions to Problems

The present disclosure provides an intraocular lens including an optical part having a mark that is detectable under illumination of a specific wavelength range outside a wavelength range of visible light, and a support part that supports the optical part, in which the mark is indicated by a geometric pattern that allows for identification of an optical center position of the optical part and information regarding posture of the optical part in an eye.

Furthermore, the present disclosure provides an intraocular lens fixing assistance system including an illumination device that irradiates an intraocular lens having an optical part having a mark that is detectable under illumination of a specific wavelength range outside a wavelength range of visible light with illumination light in at least the specific wavelength range outside the wavelength range of visible light, an image pickup device that images the intraocular lens to acquire an image by light in the specific wavelength range, an image processing apparatus that extracts the mark from the image and identifies an optical center position and posture information of the intraocular lens, and a control device that displays the optical center position and the posture information of the intraocular lens on a display device.

Moreover, the present disclosure provides an image processing apparatus including a processing unit that extracts, from an image acquired by irradiating an intraocular lens having an optical part having a mark that is detectable under illumination of a specific wavelength range outside a wavelength range of visible light with illumination light in at least the specific wavelength range outside the wavelength range of visible light, the mark from the intraocular lens, and identifies an optical center position and posture information of the intraocular lens.

Effects of the Invention

As described above, according to the present disclosure, the intraocular lens can be fixed more accurately in the eye.

Note that the effects described above are not necessarily restrictive. In addition to or in place of the effects described above, any of the effects described in the present specification or other effects that can be grasped from the present specification may be exerted.

MODE FOR CARRYING OUT THE INVENTION

Figure 1:
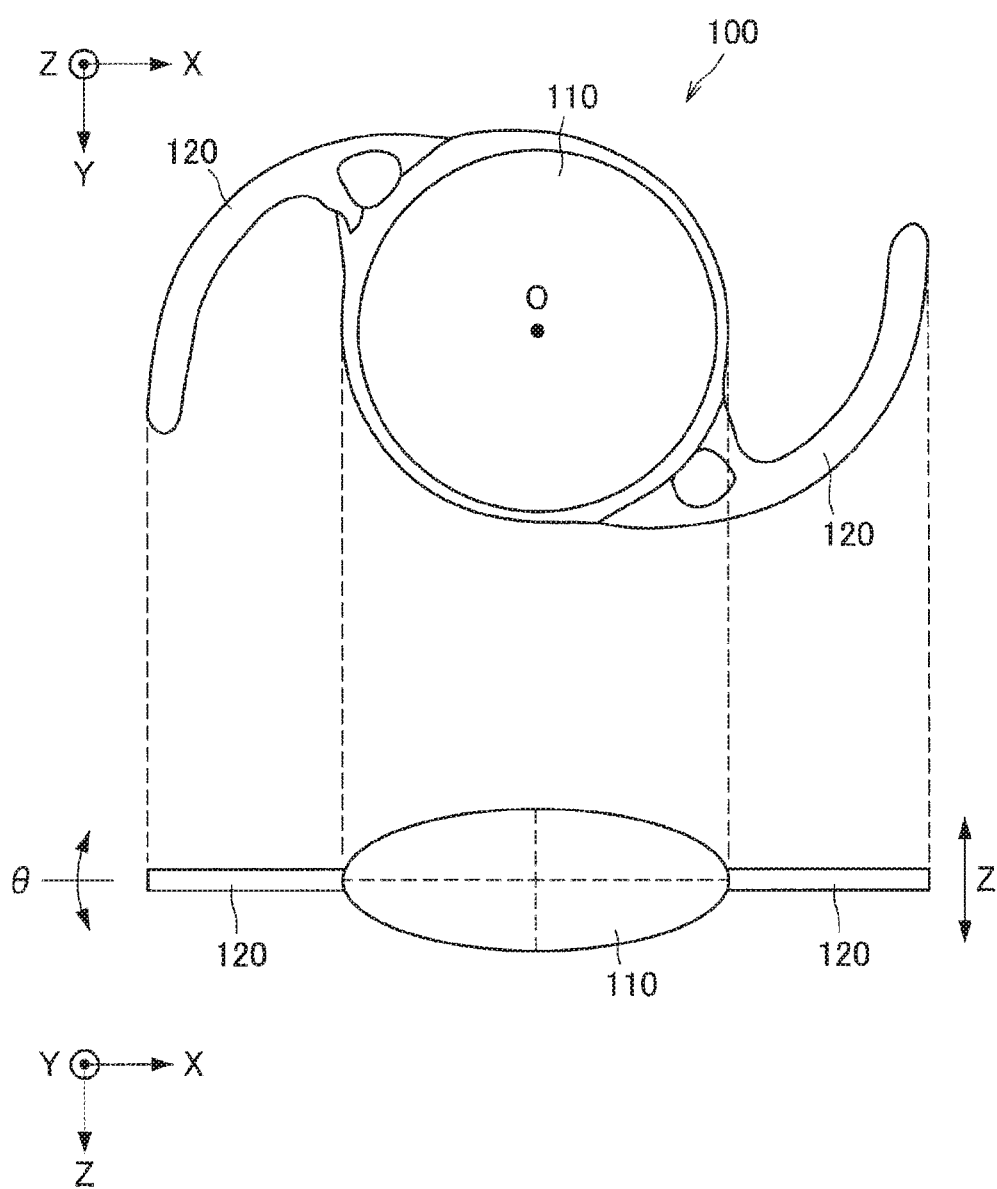
FIG. 1 is a plan view and a side view illustrating a schematic configuration of an intraocular lens according to an embodiment of the present disclosure.

A preferred embodiment of the present disclosure will be described below in detail with reference to the accompanying drawings. Note that, in the present specification and drawings, components having substantially the same functional configurations are denoted by the same reference numerals, and the description thereof will thus not be repeated.

Note that the description will be given in the following order.
1. Outline
2. System configuration
3. Intraocular lens
3.1. Characteristics of mark
(1) Characteristics of material constituting mark
(2) Marking method
3.2. Marking pattern
(1) Identification of optical center position
(2) Identification of tilt
(3) Identification of depth position
4. Utilization of intraocular lens fixing assistance system
4.1. Workflow
4.2. Application for improvement of visibility during ocular fundus observation
5. Others
6. Summary
7. Hardware configuration

[1. Outline]

Figure 2:
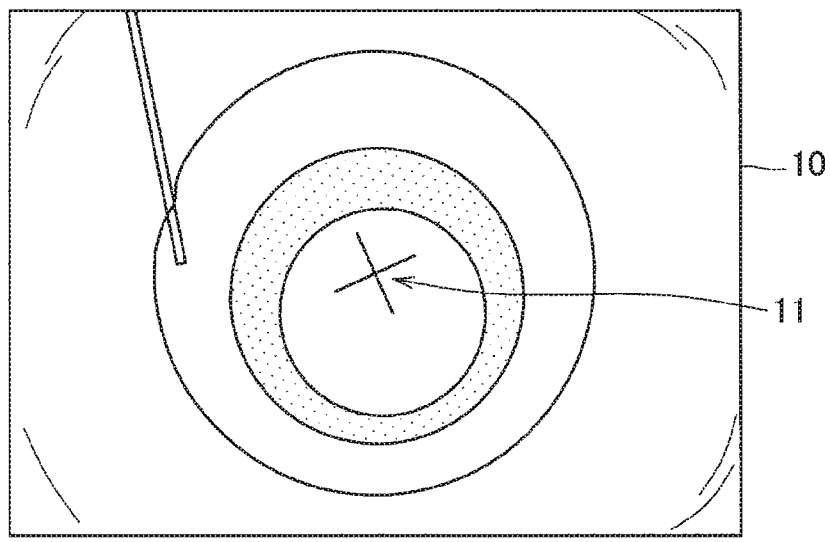
FIG. 2 is an explanatory diagram illustrating an example of information presented by an intraocular lens fixing assistance system according to the embodiment.
Figure 3:
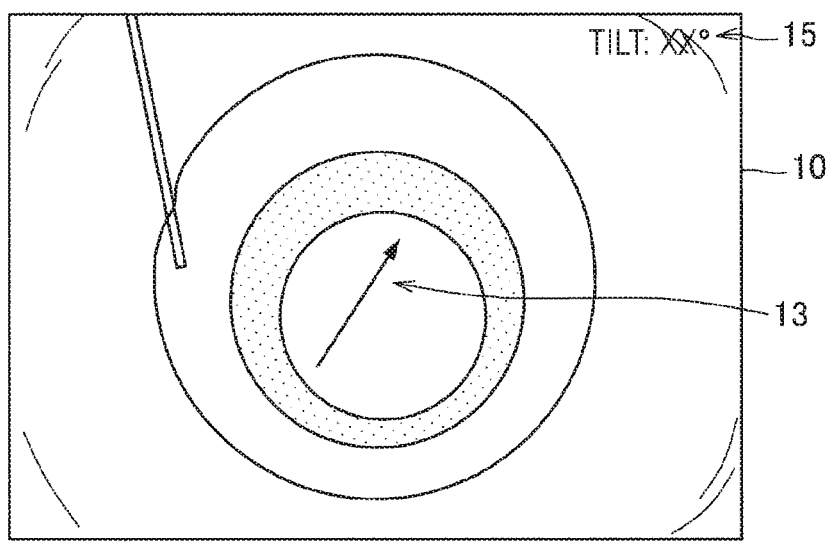
FIG. 3 is an explanatory diagram illustrating another example of information presented by the intraocular lens fixing assistance system according to the embodiment.

First, on the basis of FIGS. 1 to 3, a schematic configuration of an intraocular lens 100 according to an embodiment of the present disclosure and an example of presenting an optical center position and posture information of the intraocular lens 100 by an intraocular lens fixing assistance system will be described. FIG. 1 is a plan view and a side view illustrating the schematic configuration of the intraocular lens 100 according to the present embodiment. FIG. 2 is an explanatory diagram illustrating an example of information presented by the intraocular lens fixing assistance system according to the present embodiment. FIG. 3 is an explanatory diagram illustrating another example of information presented by the intraocular lens fixing assistance system according to the present embodiment.

As illustrated in FIG. 1, the intraocular lens 100 according to the present embodiment includes an optical part 110 and a pair of support parts 120 that support the optical part 110. The optical part 110 is a circular member that functions as a lens. The optical part 110 is a foldable member and is formed by using, for example, an acrylic material. The support parts 120 are members for placing or fixing the optical part 110 in an eye. The pair of support parts 120 are provided symmetrically with respect to an optical center position 0 of the optical part 110, as illustrated in FIG. 1, for example. The support parts 120 are also formed by using, for example, an acrylic material. The optical part 110 and the support parts 120 may be formed by using the same material.

Note that, in the following description, an optical center position of the intraocular lens 100 refers to a center position of the optical part 110 on an XY plane as illustrated in FIG. 1. Furthermore, a tilt of the intraocular lens 100 refers to a rotation about an X axis or a Y axis. For example, in a lower side of FIG. 1, a rotation about the Y axis is represented by a tilt angle θ. In addition, a depth position of the intraocular lens 100 refers to a position with respect to an eyeball in a Z-axis direction. In the lower side of FIG. 1, a depth position Z represents the depth position of the intraocular lens 100. A tilt and a depth position of an intraocular lens are collectively referred to as "posture information".

In the intraocular lens 100 according to the present embodiment, as will be described later, a mark having characteristics that allow for detection under illumination of a specific wavelength range outside a wavelength range of visible light is applied to the optical part 110. On the basis of such a mark, it is possible to identify the optical center position of the intraocular lens 100 and the posture information of the intraocular lens 100 in an eye. Then, in the intraocular lens fixing assistance system, when such an intraocular lens 100 is fixed in an eye, an optical center position and posture information of the intraocular lens 100 identified on the basis of a mark is presented to a user. With this arrangement, it is possible to assist the user in fixing the intraocular lens 100 in the eye more accurately.

For example, as illustrated in FIG. 2, a wearing state of the intraocular lens 100 in the eyeball may be displayed by superimposing a detected mark 11 of the intraocular lens 100 on an eyeball image 10, which is a visible light image acquired by a visible light image pickup device. Alternatively, as illustrated in FIG. 3, an arrow mark 13 indicating a direction of tilt of the intraocular lens 100 and a label 15 displaying a tilt angle θ may be displayed and superimposed on the eyeball image 10. At this time, the arrow mark 13 and the label 15 can be created by identifying the tilt angle and the direction of the intraocular lens 100 from the optical center position and the posture information identified on the basis of the mark of the intraocular lens 100. In this way, the intraocular lens fixing assistance system presents the wearing state of the intraocular lens 100 in the eyeball (that is, the optical center position and the posture information) in an easy-to-understand manner.

[2. System Configuration]

Figure 4:
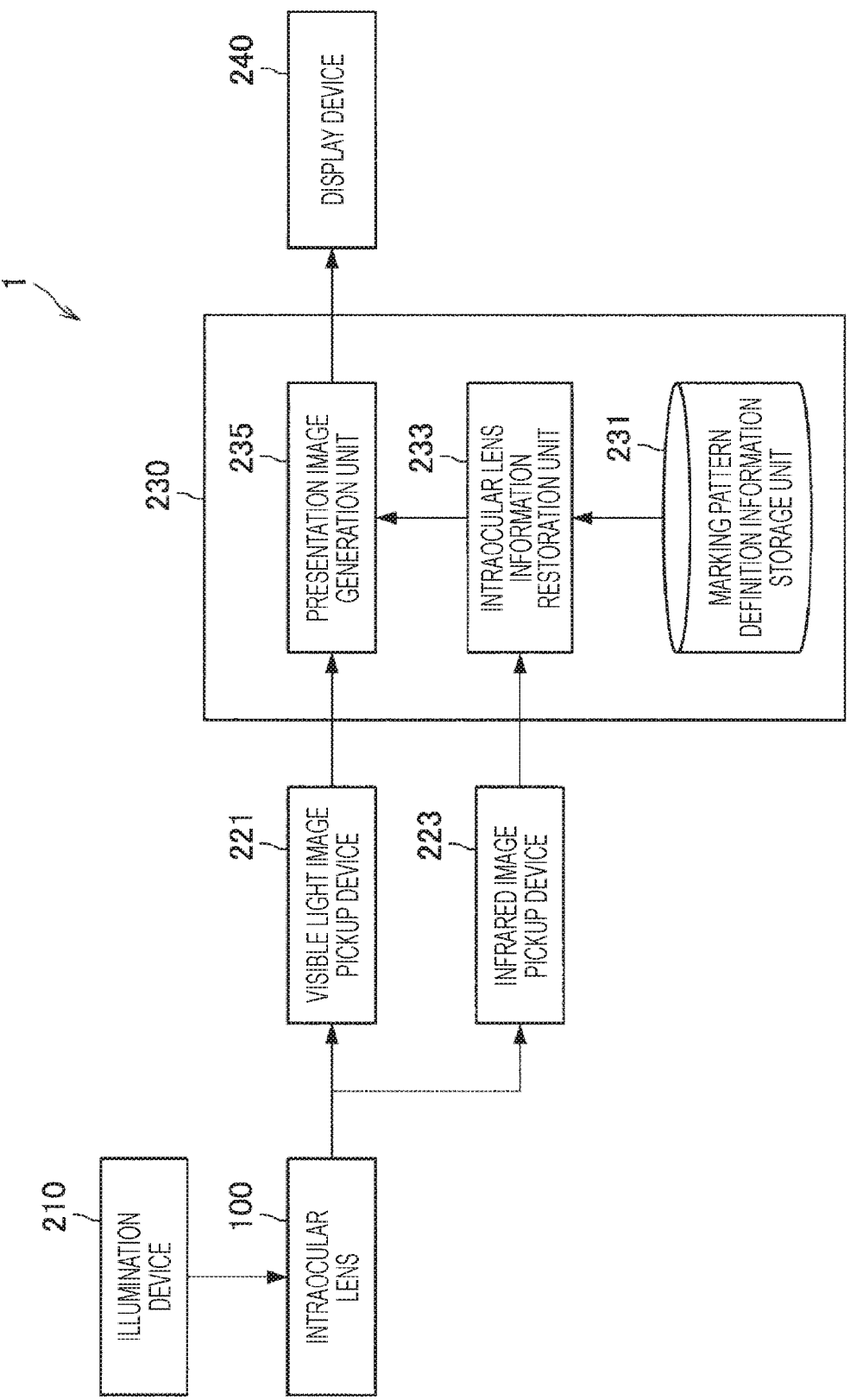
FIG. 4 is a functional block diagram illustrating a configuration example of the intraocular lens fixing assistance system according to the embodiment.

A configuration example of an intraocular lens fixing assistance system 1 according to the present embodiment will be described on the basis of FIG. 4. FIG. 4 is a functional block diagram illustrating a configuration example of the intraocular lens fixing assistance system 1 according to the present embodiment. Note that described below is a case where a mark is applied to the intraocular lens 100 with a paint that scatters infrared light, and an infrared image pickup device 220 is used to capture an image of the mark. In a case where the intraocular lens fixing assistance system 1 is incorporated in a surgical microscope, the intraocular lens fixing assistance system 1 can function as a navigation system during surgery. Furthermore, in a case where the intraocular lens fixing assistance system 1 is incorporated in an ophthalmic examination apparatus, the intraocular lens fixing assistance system 1 can also function as a system for confirming an arrangement of the intraocular lens 100 fixed in an eye after surgery. The following description assumes that the intraocular lens fixing assistance system 1 is used as the navigation system during surgery in the former case.

The intraocular lens fixing assistance system 1 according to the present embodiment includes, as illustrated in FIG. 4, an illumination device 210, a visible light image pickup device 221, an infrared image pickup device 223, an image processing apparatus 230, and a display device 240.

For observation of an eyeball of a patient wearing the intraocular lens 100, the illumination device 210 irradiates the eyeball with illumination light. The illumination device 210 emits both light in a visible light wavelength range and light in a specific wavelength range as illumination light. The light in a visible light wavelength range is emitted for acquisition of a visible light image such as an eyeball image. The light in a specific wavelength range is light other than visible light, and is emitted for acquisition of a mark applied to the intraocular lens 100. For example, the specific wavelength range is an infrared wavelength range. Note that the illumination light of the illumination device 210 is only required to include at least light in a specific wavelength range. The illumination device 210 may also serve as an illumination device for direct-view (visible light) observation, or an illumination device for direct-view observation and an illumination device for acquiring a marking may be provided separately.

The visible light image pickup device 221 is an image pickup device for capturing an image for direct-view observation. The visible light image pickup device 221 acquires a visible light image on the basis of light in a visible light wavelength range. For example, an eyeball image or the like is acquired as a visible light image. A visible light image captured by the visible light image pickup device 221 is output to a presentation image generation unit 235.

The infrared image pickup device 223 is an image pickup device for capturing an image for acquiring a mark of the intraocular lens 100. The infrared image pickup device 223 acquires an infrared image from unique absorption or scattering, fluorescence, polarization, or the like caused by the paint of the mark of the intraocular lens 100 irradiated with infrared light. An infrared image captured by the infrared image pickup device 223 is output to an intraocular lens information restoration unit 233.

The image processing apparatus 230 restores information on the basis of a mark of an intraocular lens, and generates an image to be displayed on the display device 240. As illustrated in FIG. 4, the image processing apparatus 230 includes a marking pattern definition information storage unit 231, the intraocular lens information restoration unit 233, and the presentation image generation unit 235. The marking pattern definition information storage unit 231 is a storage unit that stores in advance a pattern of the mark applied to the intraocular lens 100.

The intraocular lens information restoration unit 233 performs threshold processing or the like on an infrared image acquired by the infrared image pickup device 223, and extracts a portion having a higher or lower luminance value than its surroundings in the intraocular lens 100 to extract only an area to which a mark is applied (hereinafter, also referred to as a "marking area"). Then, the intraocular lens information restoration unit 233 calculates an optical center position and posture information of the intraocular lens 100 on the basis of the extracted marking area and marking pattern definition information. Note that a specific information restoration method will be described later. The intraocular lens information restoration unit 233 outputs the identified optical center position and posture information of the intraocular lens 100 to the presentation image generation unit 235.

The presentation image generation unit 235 combines a visible light image acquired by the visible light image pickup device 221 with the optical center position and the posture information of the intraocular lens 100 input from the intraocular lens information restoration unit 233 to generate a presentation image. The presentation image generation unit 235 outputs the generated presentation image to the display device 240.

The display device 240 is a device for displaying the presentation image generated by the presentation image generation unit 235. The display device 240 displays the presentation image to present the image to an operator. The presentation image may be an image as illustrated in FIG. 2 or 3, for example. As illustrated in FIG. 2, only an extracted mark portion may be superimposed on a visible light image so that a displacement of a pattern of the mark can be presented so as to be recognizable by the operator. Furthermore, as illustrated in FIG. 3, the direction or amount of tilt of the intraocular lens 100 calculated by the intraocular lens information restoration unit 233 may be presented as a graphic or a numerical value. At this time, the operator can repeatedly adjust the position of the intraocular lens 100 inserted in an eye while viewing the presented information, and can fix the intraocular lens 100 in the eye in an accurate position and posture.

Note that although the intraocular lens fixing assistance system 1 illustrated in FIG. 4 includes the display device 240, the present disclosure is not limited to such an example, and the display device 240 does not necessarily have to be included. For example, the intraocular lens fixing assistance system 1 may include a control device that causes a display device to display a presentation image generated by the presentation image generation unit 235, and may cause an external display device to present a presentation image. In a case where the intraocular lens fixing assistance system 1 includes the display device 240 as illustrated in FIG. 4, for example, the presentation image generation unit 235 or a separate control device (not illustrated) may cause the display device 240 to display a presentation image.

[3. Intraocular Lens]

As described above, the intraocular lens 100 according to the present embodiment has a mark applied using a material that cannot be visually recognized by the human eye such as infrared light. The mark can be acquired, in a state where the mark is irradiated with light in a specific wavelength range outside a wavelength range of visible light, by using an image pickup device such as the infrared image pickup device 223 capable of acquiring an image by light in the specific wavelength range. A mark applied to the intraocular lens 100 and its marking pattern, and a method of restoring the optical center position and the posture information of the intraocular lens from the mark will be described below.

[3.1. Characteristics of Mark]

(1) Characteristics of Material Constituting Mark

A mark to be applied to the intraocular lens 100 is applied to the intraocular lens 100 using a material having the following characteristics while satisfying conditions of materials that can be used for the intraocular lens 100, such as biocompatibility. First, the material used to apply a mark is a material that causes unique absorption or scattering, fluorescence, polarization, or the like in a specific wavelength range outside a wavelength range of visible light. Note that the fluorescence includes both fluorescence using excitation light and fluorescence without using excitation light. Here, the specific wavelength range is a wavelength range that does not interfere with not only natural light but also a wavelength range used in, for example, an ophthalmic diagnostic apparatus such as an OCT or other consumer equipment. The above-described characteristics of the material used to apply a mark do not necessarily have to be permanent. For example, processing may be performed to intentionally negate the above-described characteristics of the material by laser irradiation or the like. Alternatively, the above-described characteristics of the material used to apply a mark may be designed to disappear over time.

(2) Marking Method

A mark may be applied to the intraocular lens 100 by, for example, painting a pattern with the above-described material on a surface (front surface or back surface) of the intraocular lens 100. Alternatively, a pattern may be formed, during manufacture of the intraocular lens 100, by pouring a substance containing the above-described material into the intraocular lens 100. Moreover, for example, the surface or the inside of the intraocular lens 100 may be irradiated with a laser or the like so that a material may be transformed only at a specific portion into a material having the characteristics that the above-described material should satisfy.

[3.2. Marking Pattern]

A mark can be applied to any area in the optical part 110 of the intraocular lens 100. More specifically, in a plane (XY plane), a mark can be applied to any area in the optical part 110. Furthermore, in a depth direction (Z direction), a mark may be applied to any position from the front surface to the back surface, including the inside, of the optical part 110.

A mark may be indicated by a geometric pattern constituted by a dot or a line, and a combination of these components. That is, the components may include a straight line, a curved line, an area, and the like. Each component may be continuously filled with a material, or may be partially discontinuous. For example, the line may be a broken line. A circle, a polygon, or the like does not need to be in a closed state, and may be in an open state as in "C", in which a part thereof is missing. Examples of the geometric pattern of a mark 130 will be described below.

(1) Identification of Optical Center Position

FIGS. 5 to 16 illustrate examples of the geometric pattern of the mark 130 that allows for identification of the optical center position of the intraocular lens 100.

Figure 5:
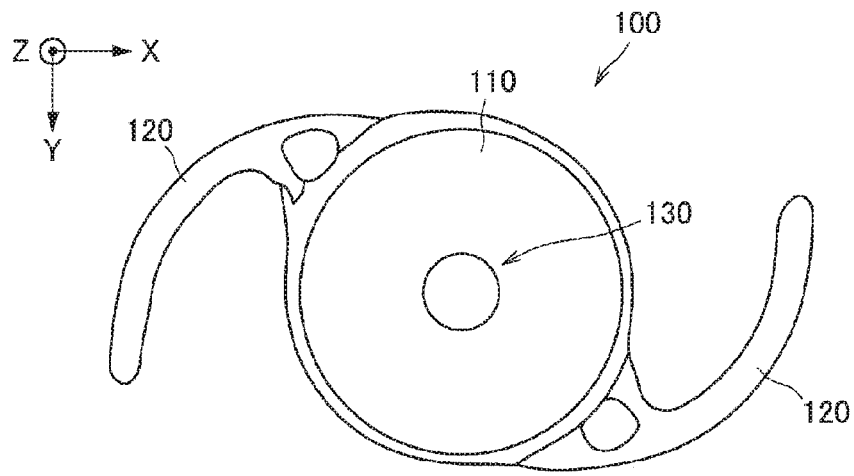
FIG. 5 is an explanatory diagram illustrating an example of a geometric pattern of a mark of the intraocular lens.
Figure 6:
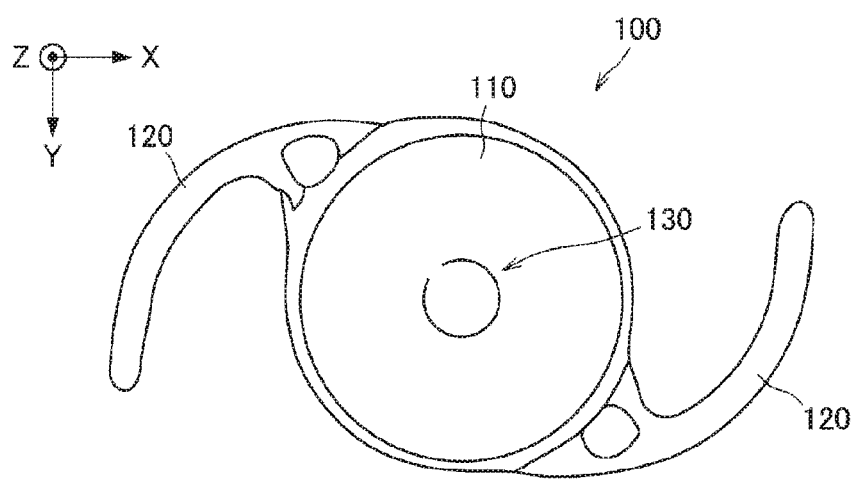
FIG. 6 is an explanatory diagram illustrating another example of the geometric pattern of the mark of the intraocular lens.

For example, as illustrated in FIGS. 5 and 6, the mark 130 may be a circle. The mark 130 in FIG. 5 is a perfect circle and is closed, or the mark 130 may be a circle that is partially missing like the mark 130 in FIG. 6. In both cases, the circle is provided so that the center point thereof, which is not actually illustrated but is identified as a virtual point, is at the optical center position of the optical part 110. Thus, the optical center position of the intraocular lens 100 can be obtained from the mark 130 by, for example, detecting the circle by Hough transform or the like from a marking area extracted by the intraocular lens information restoration unit 233 and obtaining the center point of the circle.

Figure 7:
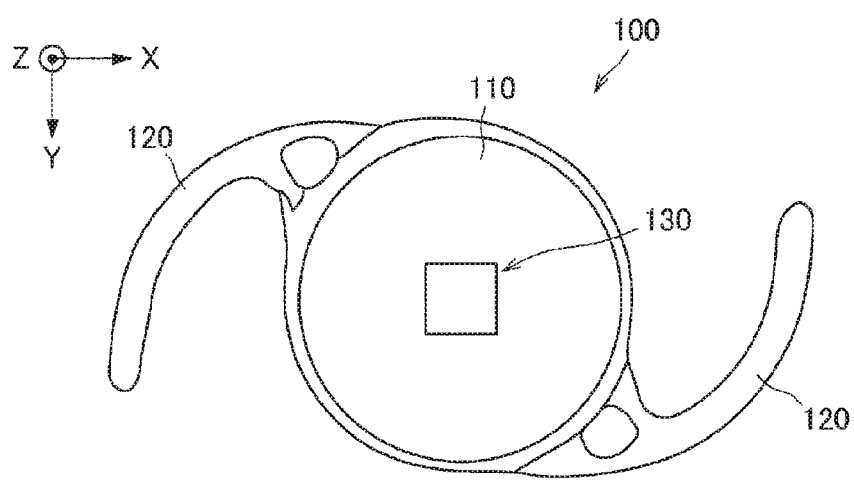
FIG. 7 is an explanatory diagram illustrating another example of the geometric pattern of the mark of the intraocular lens.
Figure 8:
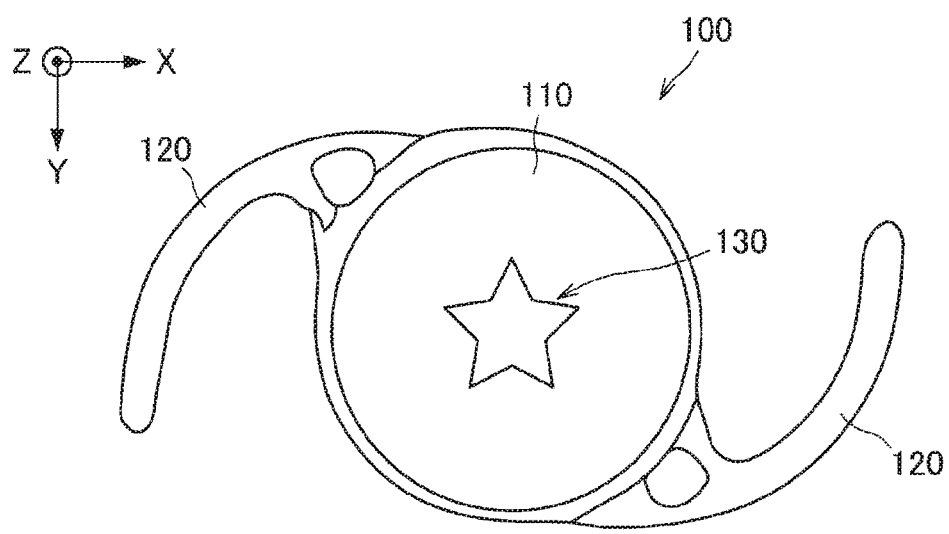
FIG. 8 is an explanatory diagram illustrating another example of the geometric pattern of the mark of the intraocular lens.

Furthermore, as illustrated in FIGS. 7 and 8, the mark 130 may be a polygon. The mark 130 in FIG. 7 is a square, and the mark 130 in FIG. 8 is a star. In both cases, the polygon is provided so that the barycentric position of the vertices of the polygon is at the optical center position of the optical part 110. Thus, the optical center position of the intraocular lens 100 can be obtained from the mark 130 by, for example, detecting vertices of the polygon from a marking area extracted by the intraocular lens information restoration unit 233 and obtaining the barycentric position of the vertices.

Figure 9:
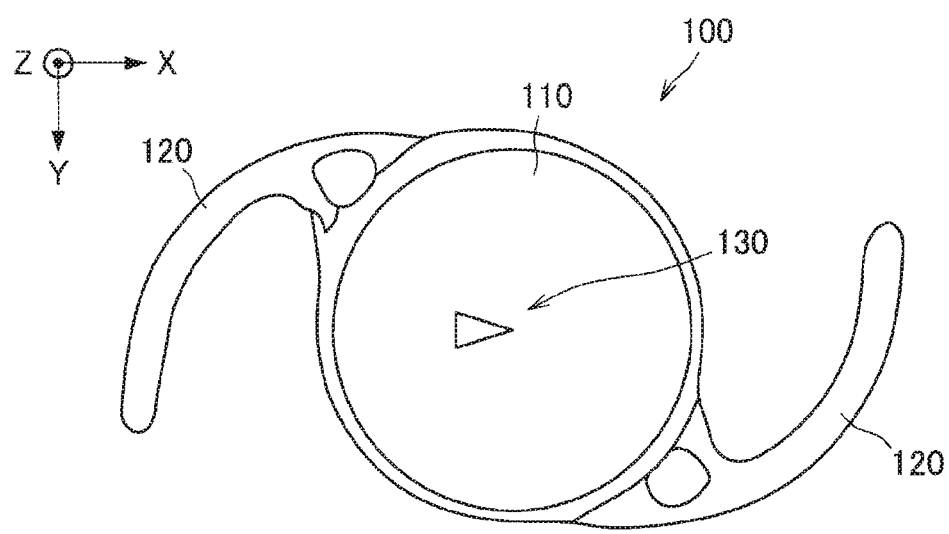
FIG. 9 is an explanatory diagram illustrating another example of the geometric pattern of the mark of the intraocular lens.
Figure 10:
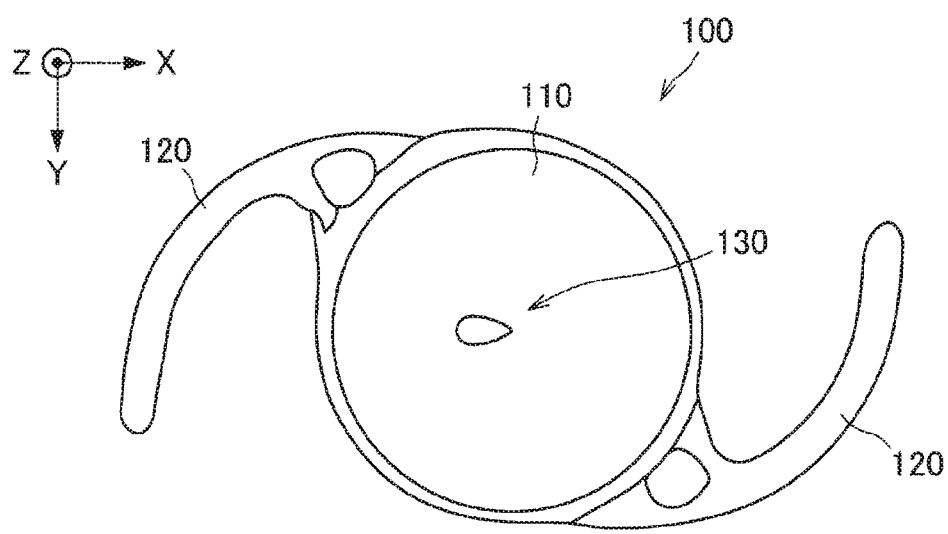
FIG. 10 is an explanatory diagram illustrating another example of the geometric pattern of the mark of the intraocular lens.

Moreover, as illustrated in FIGS. 9 to 12, the mark 130 may have a shape having one or more singular points. For example, the mark 130 in FIG. 9 is an isosceles triangle, and the mark 130 in FIG. 10 is a drop shape having one vertex.

At this time, in the mark 130 in FIG. 9, the vertex having the smallest angle can be set as a singular point, and in the mark 130 in FIG. 10, the one vertex can be set as a singular point. In addition, a point having a point with a high curvature, an end point, or the like in the geometric pattern of the mark 130 may be set as a singular point. At this time, the singular point is provided so as to be at the optical center position of the optical part 110. With this arrangement, the optical center position of the intraocular lens 100 can be obtained from the mark 130 by, for example, detecting a singular point from a marking area extracted by the intraocular lens information restoration unit 233.

Figure 11:
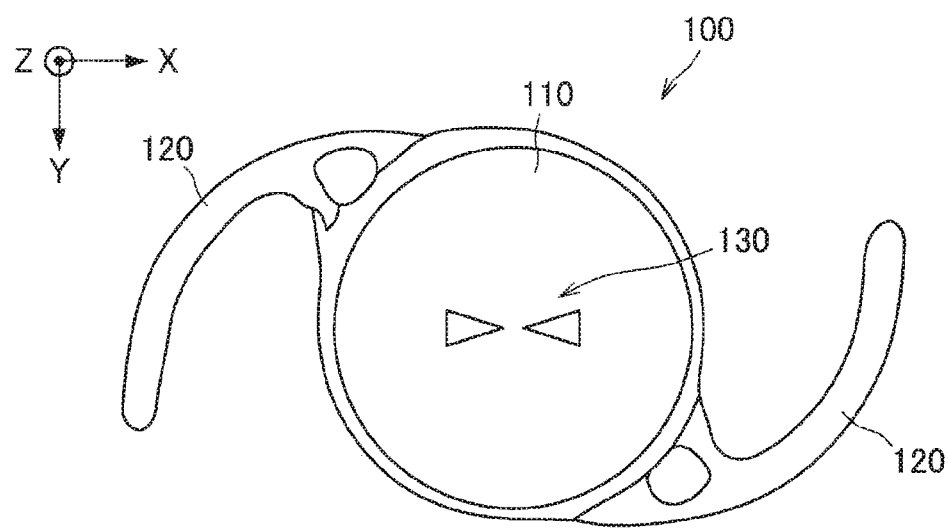
FIG. 11 is an explanatory diagram illustrating another example of the geometric pattern of the mark of the intraocular lens.
Figure 12:
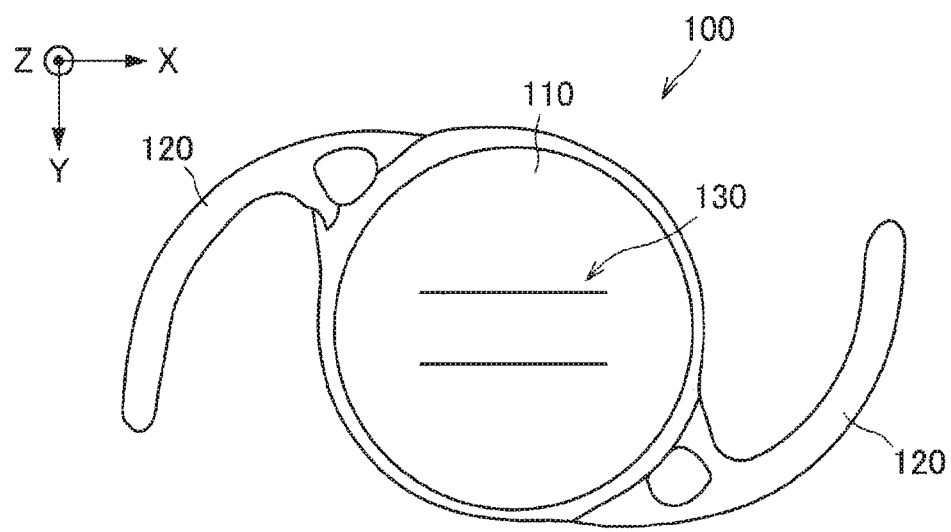
FIG. 12 is an explanatory diagram illustrating another example of the geometric pattern of the mark of the intraocular lens.

Furthermore, the mark 130 in FIG. 11 has a configuration in which two marks 130 in FIG. 9 are provided, and the mark 130 in FIG. 12 has a configuration in which two straight lines are arranged in parallel. In both cases, the two marks 130 are provided so that the barycentric position of the singular points of the two marks 130 is at the optical center position of the optical part 110. With this arrangement, the optical center position of the intraocular lens 100 can be obtained from the mark 130 by, for example, detecting singular points from marking areas extracted by the intraocular lens information restoration unit 233 and obtaining the barycentric position of the singular points.

Figure 13:
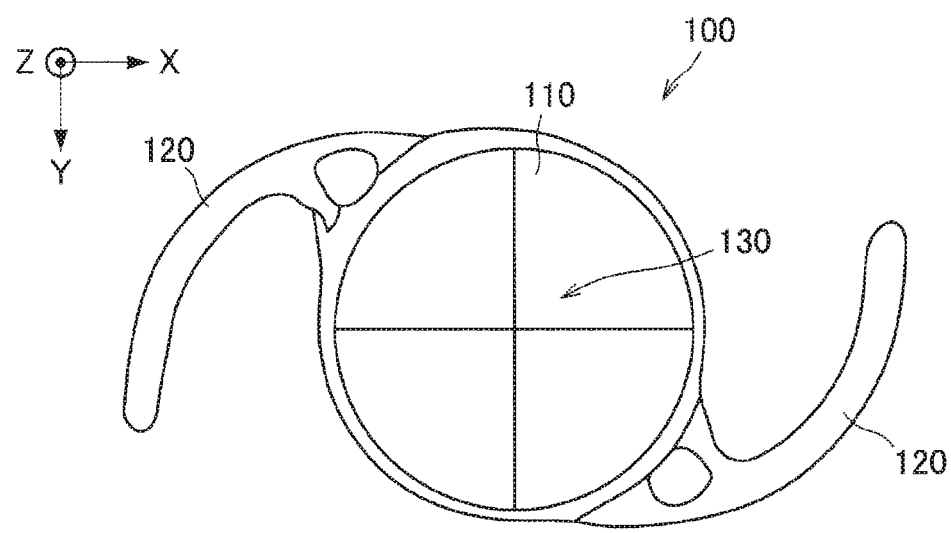
FIG. 13 is an explanatory diagram illustrating another example of the geometric pattern of the mark of the intraocular lens.
Figure 14:
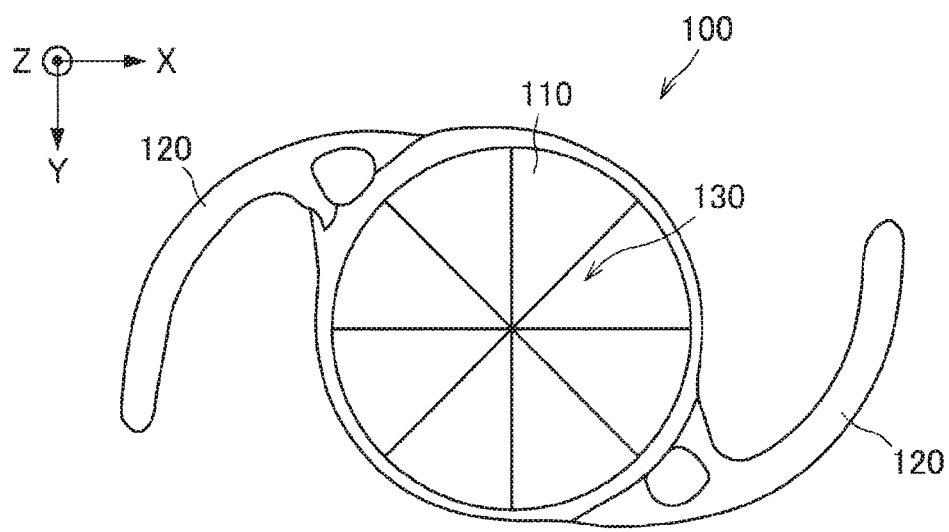
FIG. 14 is an explanatory diagram illustrating another example of the geometric pattern of the mark of the intraocular lens.

Furthermore, as illustrated in FIGS. 13 and 14, the mark 130 may be a geometric pattern in which two or more lines intersect. The mark 130 in FIG. 13 has a configuration in which two straight lines are arranged so as to pass through the optical center position of the intraocular lens 100 and be orthogonal to each other. The mark in FIG. 14 has a configuration in which three straight lines are arranged so as to pass through the optical center position of the intraocular lens 100 and be arranged at equal intervals in a circumferential direction of the optical part 110. In both cases, the intersection of a plurality of the straight lines is at the optical center position of the intraocular lens 100. Thus, the optical center position of the intraocular lens 100 can be obtained from the mark 130 by, for example, detecting straight lines by Hough transform or the like from marking areas extracted by the intraocular lens information restoration unit 233 and obtaining the intersection of the detected straight lines.

Figure 15:
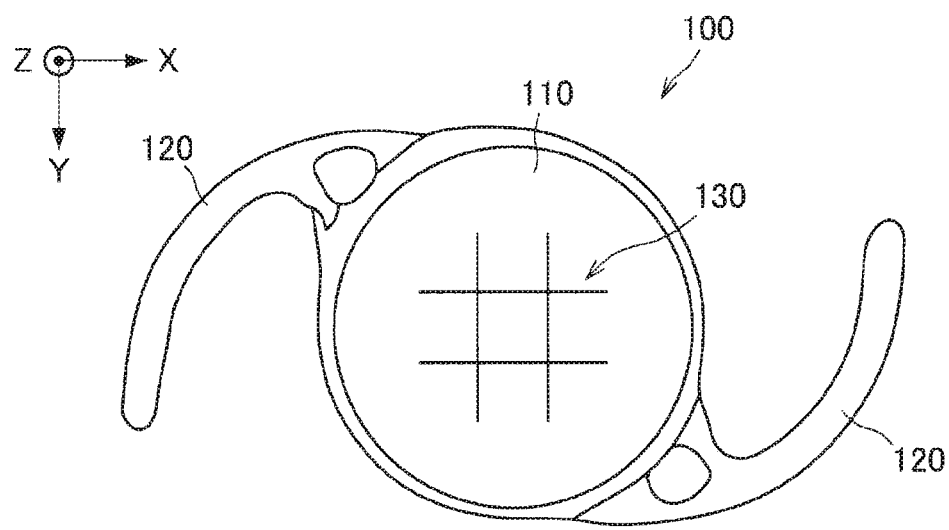
FIG. 15 is an explanatory diagram illustrating another example of the geometric pattern of the mark of the intraocular lens.

Moreover, as illustrated in FIG. 15, the mark 130 may be a lattice pattern. The mark 130 in FIG. 15 is a geometric pattern that surrounds the optical center position of the intraocular lens 100 with four straight lines. The center of the lattice is the optical center position of the intraocular lens 100. Thus, the optical center position of the intraocular lens 100 can be obtained from the mark 130 by, for example, detecting straight lines by Hough transform or the like from marking areas extracted by the intraocular lens information restoration unit 233 and obtaining the barycentric position of four intersection coordinates of the detected straight lines.

Figure 16:
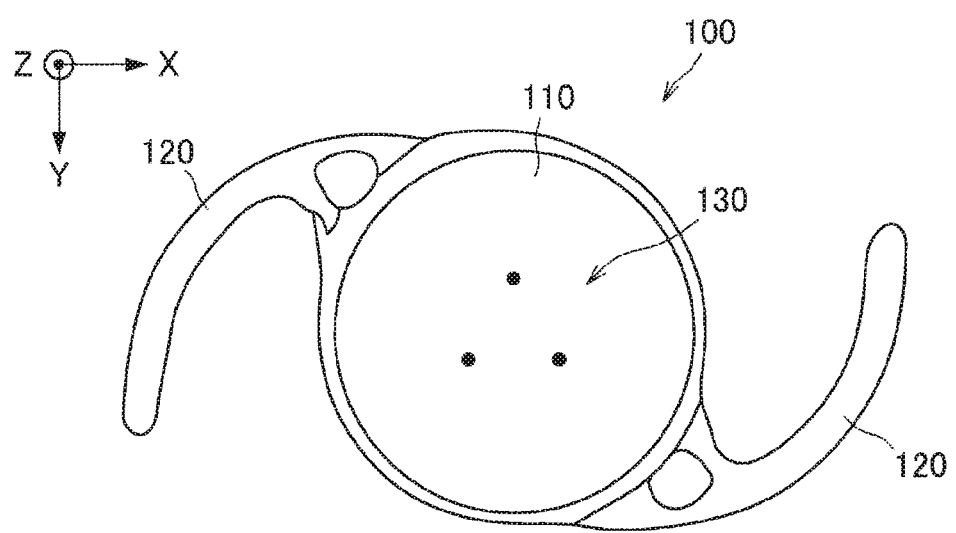
FIG. 16 is an explanatory diagram illustrating another example of the geometric pattern of the mark of the intraocular lens.

Furthermore, as illustrated in FIG. 16, the mark 130 may be a dot pattern. The mark 130 in FIG. 16 is constituted by three dots, and the dots are arranged so that the barycentric position of the dots is at the optical center position of the intraocular lens 100. Thus, the optical center position of the intraocular lens 100 can be obtained from the mark 130 by, for example, obtaining the barycentric position of areas containing the dots from marking areas extracted by the intraocular lens information restoration unit 233 and further obtaining the center of gravity of the barycentric positions.

(2) Identification of Tilt

The tilt of the intraocular lens 100 can be identified by a distortion of the shape of the mark 130 or a misalignment between a plurality of the marks 130 arranged at different positions in the depth direction of the optical part 110.

Examples of the geometric pattern of the mark 130 in which the tilt of the intraocular lens 100 can be identified from a distortion of the shape of the mark 130 include, for example, the circles illustrated in FIGS. 5 and 6, polygons as illustrated in FIGS. 7 and 8, the lattice pattern in FIG. 15, and the dot pattern in FIG. 16.

For example, in a case where the mark 130 is a circle as illustrated in FIGS. 5 and 6, ellipse fitting processing is performed on a marking area extracted by the intraocular lens information restoration unit 233. The amount of tilt can be calculated from the ratio of the major axis length to the minor axis length, and the direction of tilt can be calculated from the directions of the major axis and the minor axis. Furthermore, for example, in a case where the mark 130 is a polygon as illustrated in FIGS. 7 and 8, vertices of the polygon are detected from a marking area extracted by the intraocular lens information restoration unit 233. The amount of tilt and the direction of tilt can be obtained on the basis of a relationship between distances between the vertices. Moreover, in the cases of the lattice pattern in FIG. 15 and the dot pattern in FIG. 16, the amount of tilt and the direction of tilt can be obtained as in the case of a polygon.

Figure 17:
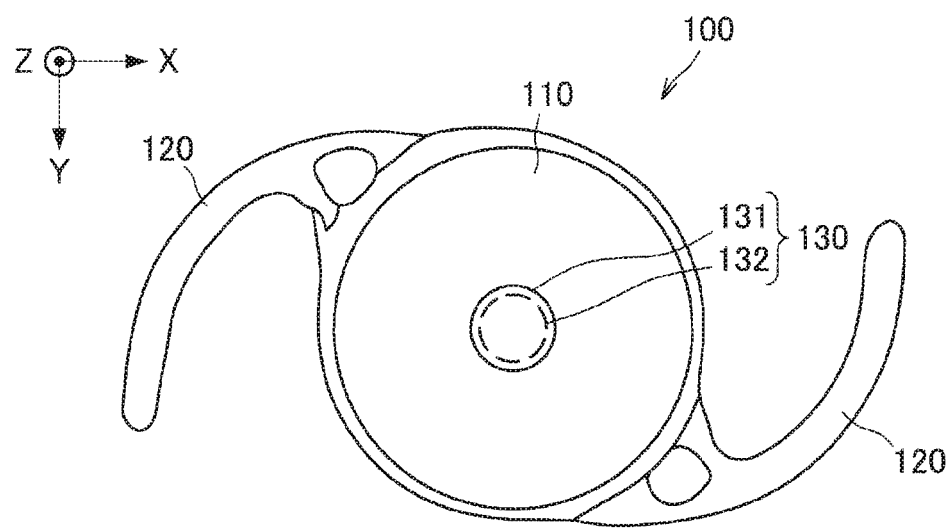
FIG. 17 is an explanatory diagram illustrating a case where a tilt of the intraocular lens is identified on the basis of a misalignment between a plurality of marks arranged at different positions in a depth direction.
Figure 17:
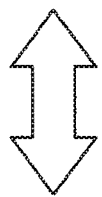
Figure 17:
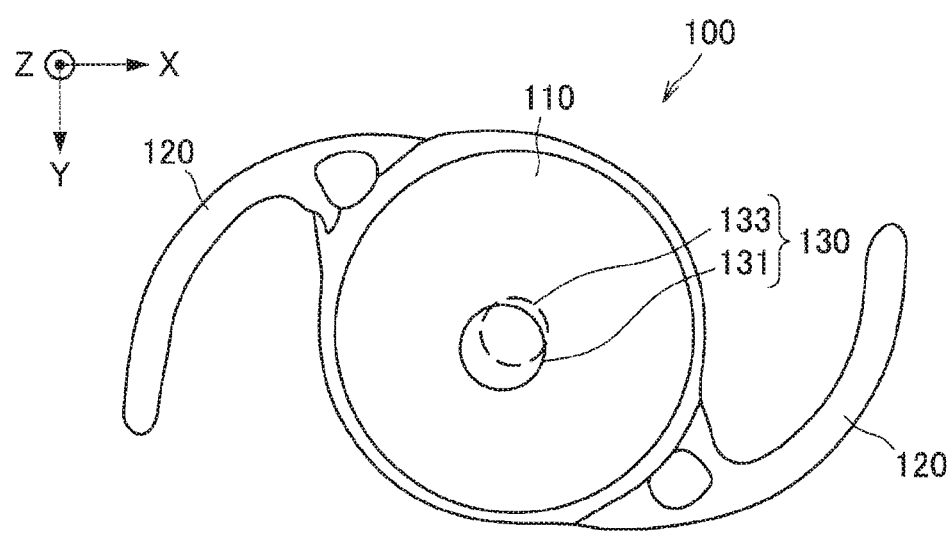

On the other hand, in a case where the tilt of the intraocular lens 100 is identified on the basis of a misalignment between a plurality of the marks 130 arranged at different positions in the depth direction, for example, two circular marks 131 and 133 may be provided as illustrated in FIG. 17. The mark 131 is arranged on the front surface side of the optical part 110, and the mark 133 is arranged on the back surface side of the optical part 110. The marks 131 and 133 are both arranged so that their centers are at the optical center position of the intraocular lens 100. Thus, when the intraocular lens 100 is not tilted, the circles of the two marks 131 and 133 are concentric as illustrated in an upper side of FIG. 17. On the other hand, when the intraocular lens 100 is tilted, the center position of the circular mark 131 on the front surface and the center position of the circular mark 133 on the back surface are displaced from each other as illustrated in a lower side of FIG. 17. On the basis of this displacement between the center positions, the amount of tilt and the direction of tilt of the intraocular lens 100 can be obtained.

In this way, the tilt (amount of tilt and direction of tilt) of the intraocular lens 100 can be identified from the mark 130 of the intraocular lens 100.

(3) Identification of Depth Position

Figure 18:
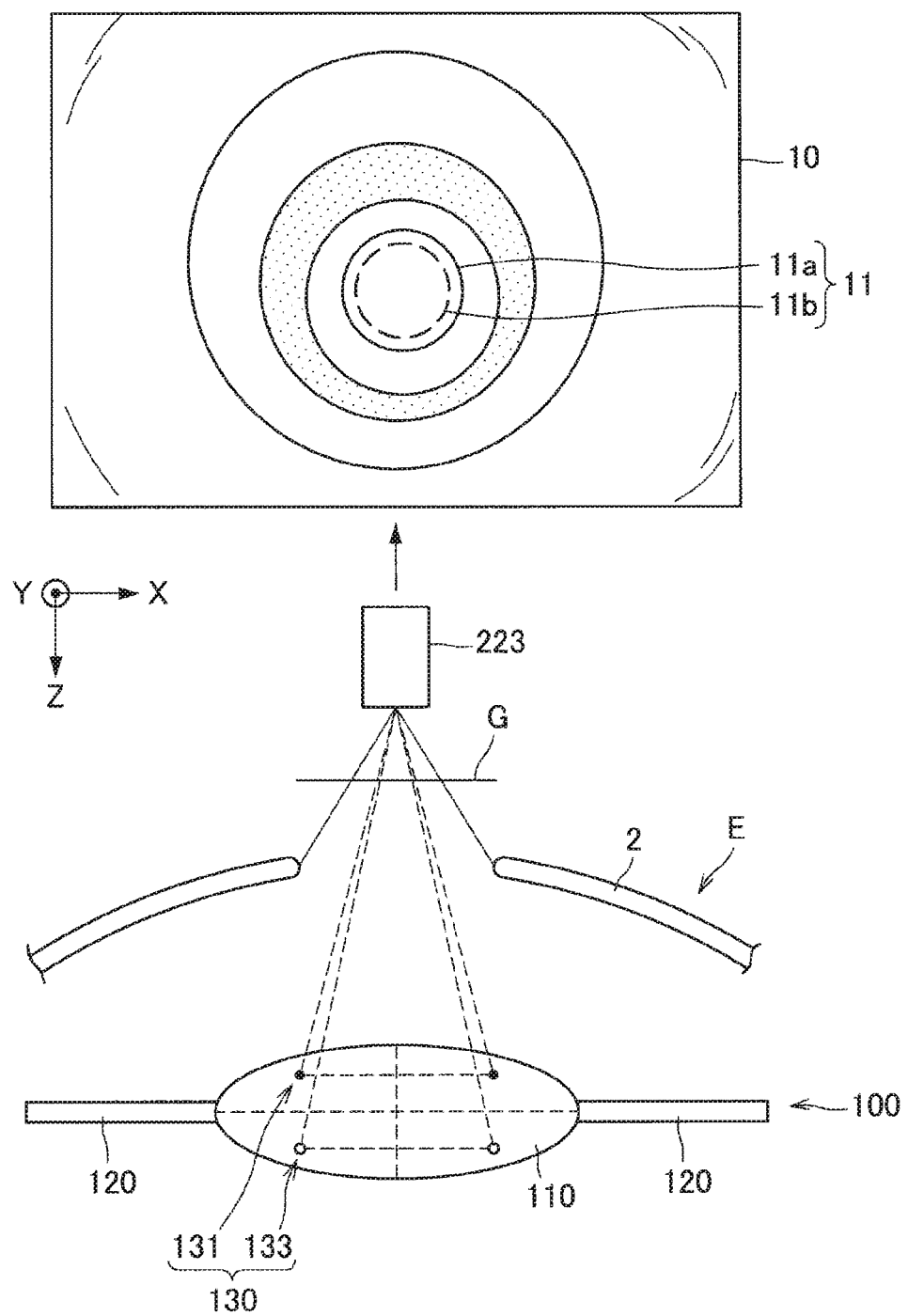
FIG. 18 is an explanatory diagram illustrating a case where a depth position of the intraocular lens is identified on the basis of a misalignment between a plurality of marks arranged at different positions in the depth direction.
Figure 19:
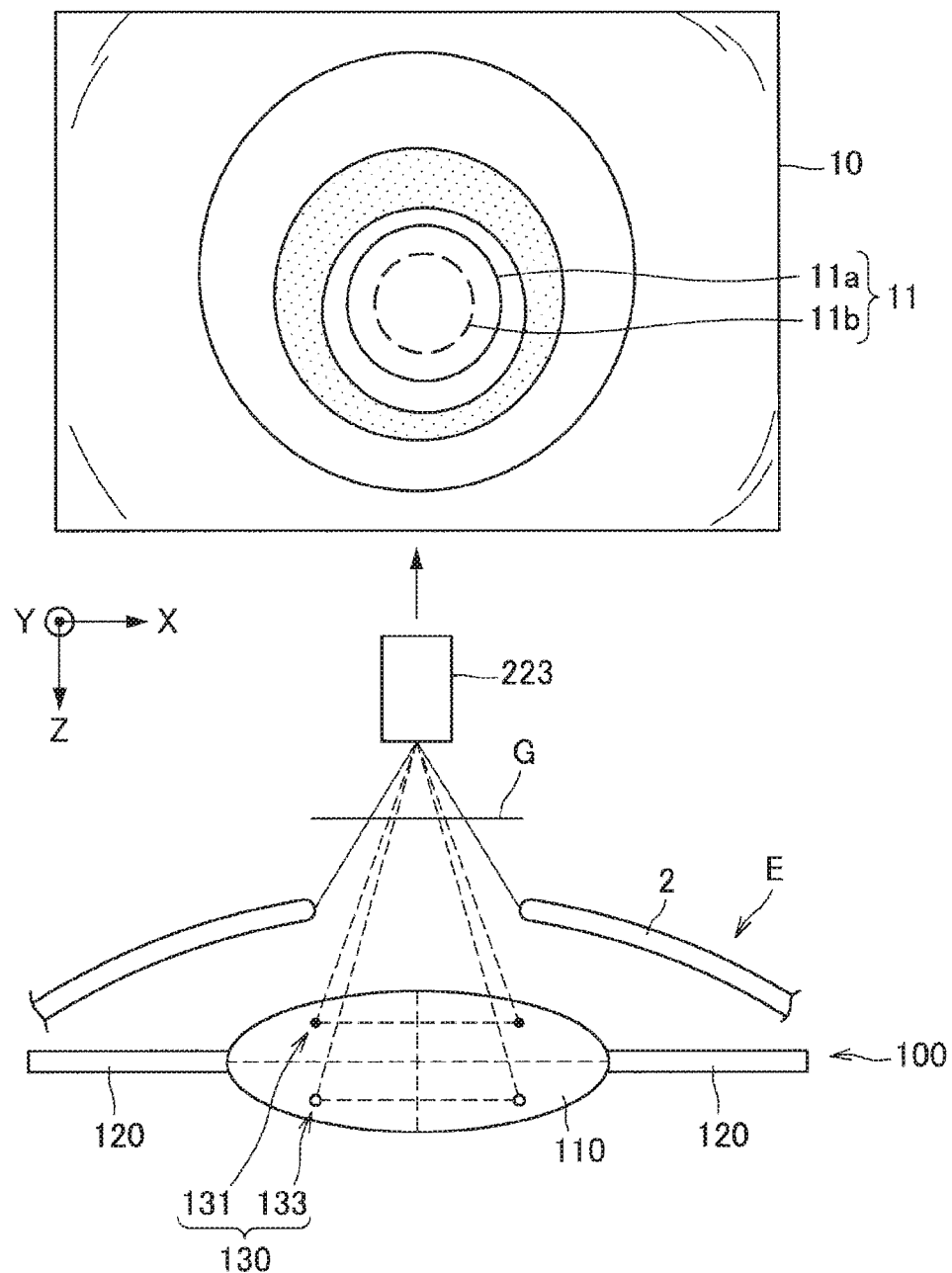
FIG. 19 is an explanatory diagram illustrating a case where the depth position of the intraocular lens is identified on the basis of a misalignment between the plurality of marks arranged at different positions in the depth direction.

The depth position of the intraocular lens 100 can be identified on the basis of a positional relationship between a plurality of the marks 130 arranged at different positions in the depth direction of the optical part 110. The infrared image pickup device 223 that captures images from outside an eye can observe both the mark 131 on the front surface and the mark 133 on the back surface. At this time, as illustrated in FIGS. 18 and 19, when the position of the intraocular lens 100 with respect to the infrared image pickup device 223 changes, a difference in radius between a circle on the front surface (outer mark 11a) and a circle on the back surface side (inner mark 11b) changes in the images. For example, the intraocular lens 100 is closer to the infrared image pickup device 223 in FIG. 19 than in FIG. 18. At this time, the difference in radius between the circular marks 11a and 11b in the image increases as the intraocular lens 100 is closer to the infrared image pickup device 223.

With this arrangement, on the basis of a positional relationship between the marks 131 and 133 detected from an infrared image acquired by the infrared image pickup device 223 and an organ serving as a reference (for example, an iris 2), a relative distance between the iris 2 and the intraocular lens 100 can be grasped.

[4. Utilization of Intraocular Lens Fixing Assistance System]

[4.1. Workflow]

An example of a workflow from before surgery to after surgery utilizing the intraocular lens fixing assistance system 1 according to the present embodiment will be described.

First, in a preoperative examination, a power of the intraocular lens 100 and the like are selected and a simulation is performed on the basis of information obtained by an examination apparatus to make a plan for an optimal position to place the intraocular lens 100 in accordance with a shape of an eyeball of a patient. Next, the intraocular lens 100 to which the mark 130 has been applied is manufactured, the mark 130 being specialized for information required for highly accurate positioning according to the plan. The mark 130 may be applied to the intraocular lens 100 that has already been manufactured.

During surgery, the intraocular lens fixing assistance system 1 is used to arrange the intraocular lens at a predetermined position that has been planned, on the basis of the information obtained from the mark 130 of the intraocular lens 100. Furthermore, in a case where, for example, corrected visual acuity does not improve as expected in a postoperative examination or the like, it is possible that the intraocular lens 100 is misaligned. Thus, the intraocular lens fixing assistance system 1 can be used to confirm whether or not the intraocular lens 100 fixed in the eye is misaligned. In a case where the intraocular lens 100 is misaligned, it is possible to consider performing a procedure for correcting the misalignment of the intraocular lens 100 or the like.

[4.2. Application for Improvement of Visibility During Ocular Fundus Observation]

Figure 20:
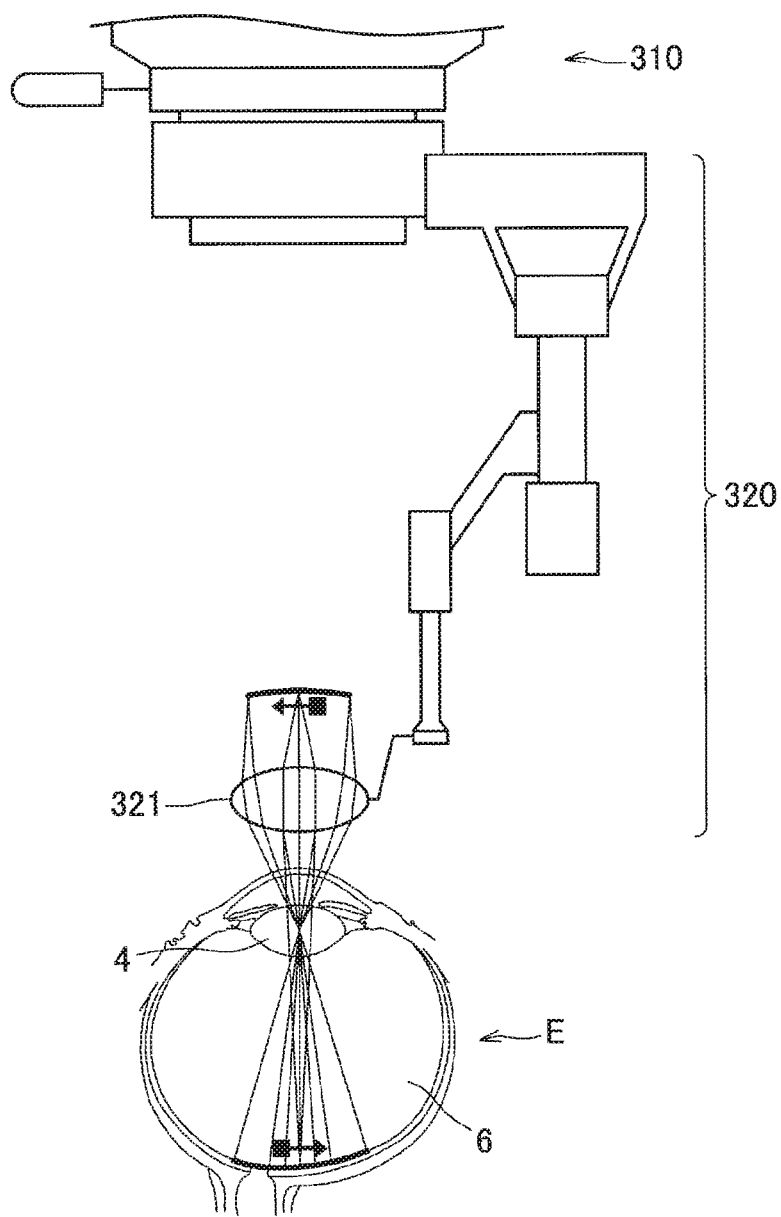
FIG. 20 is an explanatory diagram illustrating an example of a surgical microscope in which a front-end lens is set using a non-contact wide-angle observation system.

In retinal-vitreous surgery (ocular fundus surgery), an ocular fundus is observed using, in addition to a surgical microscope 310, a special lens for ocular fundus observation (hereinafter referred to as a "front-end lens") 321 arranged close to or in contact with an eyeball E as illustrated in FIG. 20. FIG. 20 illustrates an example in which a non-contact wide-angle observation system 320 is used to set the front-end lens 321 for observation of the ocular fundus. Retinal-vitreous surgery may be performed also on a patient with the intraocular lens 100 inserted. At this time, in a case where an optical axis of the inserted intraocular lens 100 and an optical axis of the front-end lens 321 are not aligned with each other, visibility of the ocular fundus observation deteriorates. It is known to be remarkable especially in a case of an intraocular lens called a multifocal intraocular lens.

Thus, the intraocular lens fixing assistance system 1 according to the present embodiment can be used to grasp the optical center position and posture information of the intraocular lens 100 inserted into an eye of a patient. By using the optical center position and the posture information of the intraocular lens 100, the position of the front-end lens 321 can be easily adjusted so that their optical axes are aligned with each other. The position of the front-end lens 321 may be adjusted by adjusting the position of the surgical microscope 310 in a case of the wide-angle observation system 320 attached to the surgical microscope 310 as illustrated in FIG. 20, for example. Furthermore, in a case where the front-end lens 321 is a contact lens held by a hand (finger), an operator may manually adjust the position of the front-end lens 321.

Figure 21:
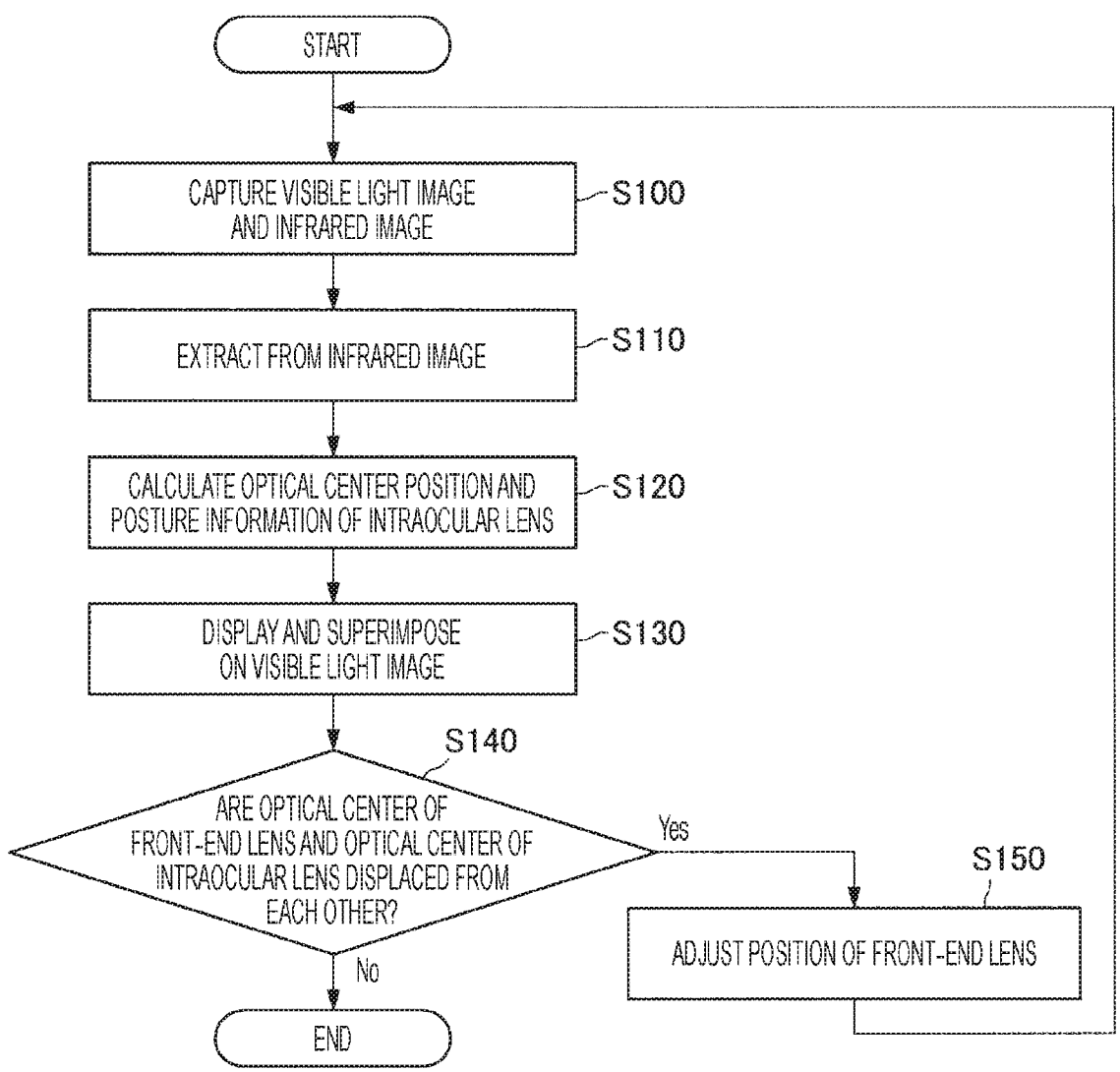
FIG. 21 is a flowchart illustrating processing of adjusting a position of the front-end lens using the intraocular lens fixing assistance system according to the embodiment.

Processing of adjusting the position of the front-end lens 321 using the intraocular lens fixing assistance system 1 according to the present embodiment is illustrated in FIG. 21. FIG. 21 is a flowchart illustrating the processing of adjusting the position of the front-end lens 321 using the intraocular lens fixing assistance system 1 according to the present embodiment.

As illustrated in FIG. 20, first, the illumination device 210 irradiates an eye in which the intraocular lens 100 has been inserted with illumination light, the visible light image pickup device 221 acquires a visible light image, and the infrared image pickup device 223 acquires an infrared image (S100). Next, the intraocular lens information restoration unit 233 extracts the mark 130 of the intraocular lens 100 from the infrared image (S110). Then, the optical center position and posture information of the intraocular lens 100 is calculated from the shape of the extracted mark 130 (S120). Thereafter, the presentation image generation unit 235 superimposes information indicating the optical center position and the posture information of the intraocular lens 100 on the visible light image to generate a presentation image as illustrated in FIG. 2 or 3, for example, and the presentation image is displayed on the display device 240 (S130).

Then, on the basis of the presentation image, it is determined whether or not the optical center of the front-end lens 321 and the optical center of the intraocular lens 100 are displaced from each other (S140). If the optical center of the front-end lens 321 and the optical center of the intraocular lens 100 are displaced from each other, the position of the front-end lens 321 is adjusted (S150), and then the processing from step S100 is repeated.

In this way, in retinal-vitreous surgery, using the intraocular lens fixing assistance system 1 according to the present embodiment improves the visibility of ocular fundus observation during retinal-vitreous surgery.

[5. Others]

The intraocular lens 100 according to the present embodiment has the mark 130 that has been applied to enable acquisition of the optical center position and posture information, but the present disclosure is not limited to such an example. For example, information regarding characteristics or manufacturing of the intraocular lens 100 may be embedded as a separate mark (second mark).

Specifically, for example, information regarding the lens shape such as the spherical power, size, and curvature or the material of the lens may be able to be identified by the second mark as a lens characteristic. Furthermore, for example, information regarding manufacturing such as a serial number indicating a manufacturer, a manufacturing time, a place, a lot, or the like may be able to be identified by the second mark. For example, a character string may be directly marked and applied as the second mark, or a geometric pattern in which information is encoded as in a two-dimensional code such as a barcode or a QR code (registered trademark) may be applied as the second mark.

[6. Summary]

The intraocular lens 100 according to the present embodiment and the intraocular lens fixing assistance system 1 using the intraocular lens 100 have been described above. Using this intraocular lens 100 makes it possible to confirm, during intraocular lens insertion surgery, the optical center position and posture information of the intraocular lens 100 being inserted, and provide assistance for accurate placement or fixation of the intraocular lens 100, and an improvement in visual function can be expected.

Figure 22:
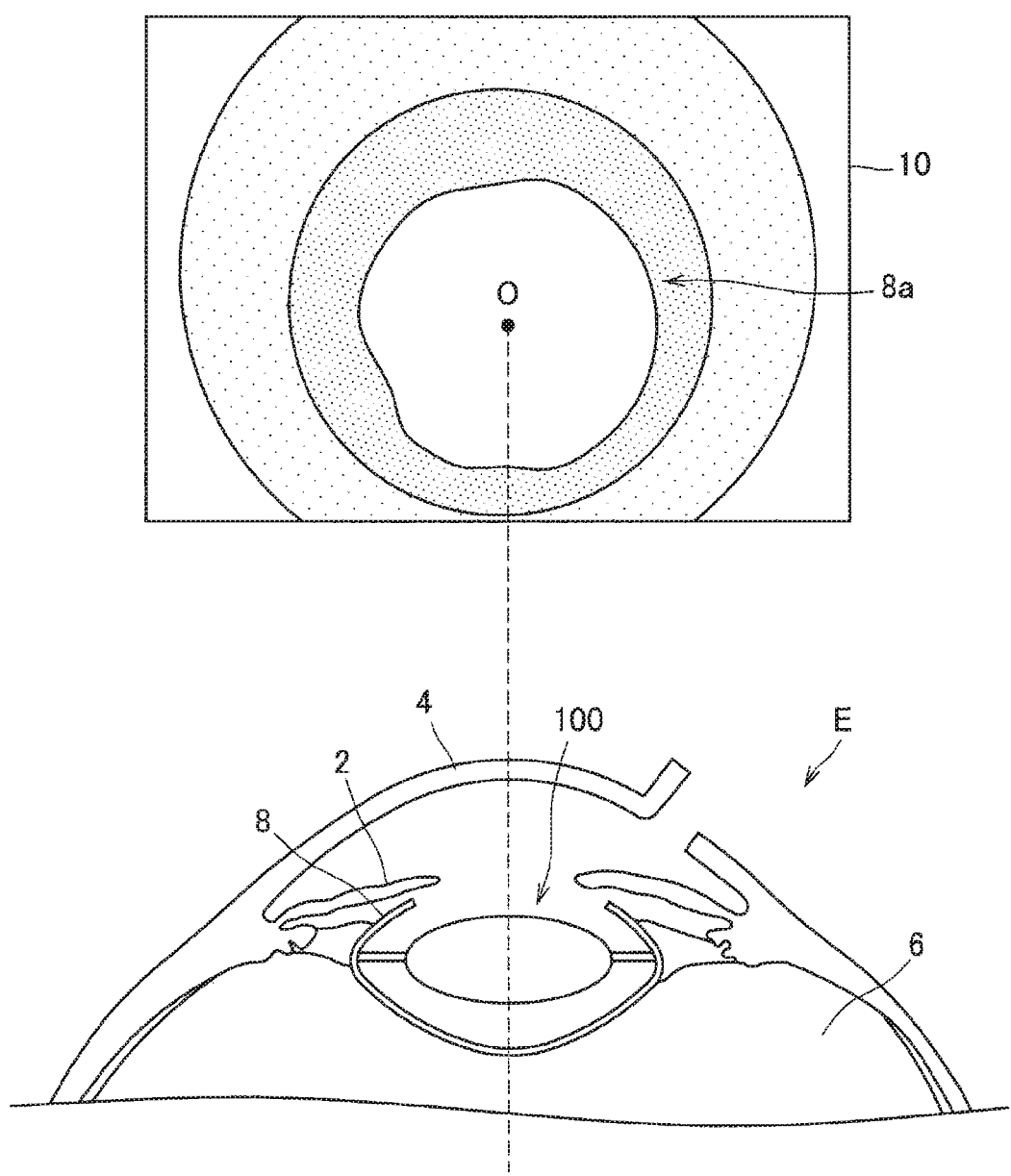
FIG. 22 is an explanatory diagram illustrating a relationship between an anterior capsule incision circle and an optical center of the intraocular lens in cataract surgery.

By knowing the optical center position of the intraocular lens 100, for example, in cataract surgery, the position of the intraocular lens 100 can be corrected so that an anterior capsule incision circle 8a (incision portion of an anterior surface of a lens during cataract surgery) and the optical center of the intraocular lens 100 are aligned with each other as illustrated in FIG. 22. Alternatively, in a case where the anterior capsule incision circle 8a is not in the right position or size, it can be used as a material for determining whether or not an additional anterior capsule incision is necessary. With this arrangement, an improvement in postoperative visual function can be expected.

Furthermore, by knowing the tilt of the intraocular lens 100, it is possible to grasp whether or not the optical axis of the intraocular lens 100 is tilted with respect to an eye axis. Thus, in a case where the intraocular lens 100 is tilted, it is possible to immediately correct the tilt so that the intraocular lens 100 is placed in a correct position. With this arrangement, an improvement in postoperative visual function can be expected.

Moreover, by knowing the depth position of the intraocular lens 100, for example, in an intraocular lens for refractive correction (ICL) fixed in a ciliary sulcus, whether or not the lens size is appropriate can be determined on the basis of the depth position of the intraocular lens 100 with respect to the lens. With this arrangement, in a case where the lens size is unsuitable, it is possible to take an action such as replacing the lens on the spot.

Furthermore, since the optical center position and the posture information of the inserted intraocular lens 100 can be confirmed in postoperative follow-up observation or the like, it is also possible to detect a displacement of the intraocular lens 100 that has occurred after surgery. With this arrangement, it is possible to provide, in a case where improvement in visual function is insufficient, a material for identifying a cause, determining a necessity of further surgery, or the like. For example, the intraocular lens 100 may be displaced after surgery due to breakage of a securing suture. In this case as well, it is possible to take action early.

Moreover, during retinal-vitreous surgery on an eye into which an intraocular lens has been inserted, information regarding the position and posture of the inserted intraocular lens can be confirmed, and this makes it possible to grasp a positional relationship with a front-end lens used for ocular fundus observation. With this arrangement, placement of the front-end lens can be optimized, and thus an improvement in visibility of ocular fundus observation can be expected.

Furthermore, during preoperative or postoperative examination, it is possible to view characteristics and manufacturing information of an intraocular lens, and it is therefore possible to acquire information regarding the power of the intraocular lens 100 that has been inserted at a time of adding an intraocular lens or replacing the intraocular lens. With this arrangement, preoperative planning can be performed more accurately. Furthermore, at a time of removing the intraocular lens 100, it is possible to obtain information regarding the shape of the inserted intraocular lens 100, and this makes it possible to grasp the structure and the like of the support parts 120 and easily take out the intraocular lens 100. Moreover, at a time of removing the intraocular lens 100, it is possible to obtain information regarding the material of the inserted intraocular lens 100, and this makes it possible to grasp in advance whether or not the intraocular lens 100 can be broken by a cutter or the like, for example.

[7. Hardware Configuration]

Figure 23:
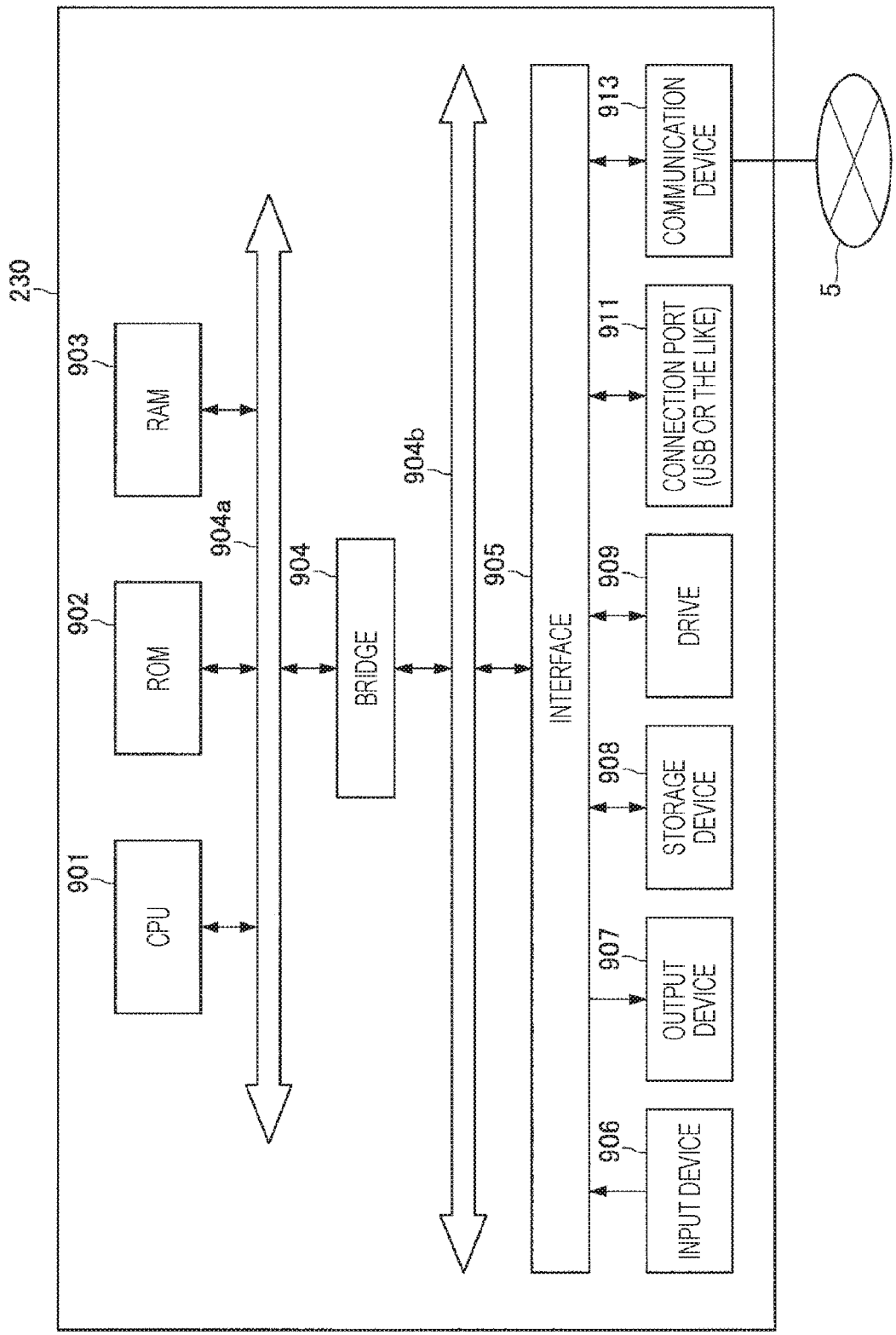
FIG. 23 is a hardware configuration diagram illustrating a hardware configuration of an image processing apparatus according to the embodiment.

A hardware configuration example of the image processing apparatus 230 of the intraocular lens fixing assistance system 1 according to the above embodiment will be described. FIG. 23 is a hardware configuration diagram illustrating a hardware configuration of the image processing apparatus 230 according to the present embodiment.

The image processing apparatus 230 according to the present embodiment can be constituted by a processing apparatus such as a computer as described above. As illustrated in FIG. 23, the image processing apparatus 230 includes a central processing unit (CPU) 901, a read only memory (ROM) 902, a random access memory (RAM) 903, and a host bus 904a. Furthermore, the image processing apparatus 230 includes a bridge 904, an external bus 904b, an interface 905, an input device 906, an output device 907, a storage device 908, a drive 909, a connection port 911, and a communication device 913.

The CPU 901 functions as an arithmetic processing device and a control device, and controls overall operations in the image processing apparatus 230 according to various programs. Furthermore, the CPU 901 may be a microprocessor. The ROM 902 stores a program used by the CPU 901, an arithmetic parameter, and the like. The RAM 903 temporarily stores a program used for execution by the CPU 901, a parameter that changes during the execution as appropriate, and the like. They are connected to each other by the host bus 904a constituted by a CPU bus or the like.

The host bus 904a is connected to the external bus 904b such as a peripheral component interconnect/interface (PCI) bus via the bridge 904. Note that the host bus 904a, the bridge 904, and the external bus 904b do not necessarily have to have separate configurations, and these functions may be included in one bus.

The input device 906 is constituted by input means such as a mouse, a keyboard, a touch panel, a button, a microphone, a switch, and a lever for a user to input information, an input control circuit that generates an input signal on the basis of an input by the user and outputs the input signal to the CPU 901, and the like. The output device 907 includes, for example, a display device such as a liquid crystal display (LCD) device, an organic light emitting diode (OLED) device, and a lamp; and an audio output device such as a speaker.

The storage device 908 is an example of a storage unit of the image processing apparatus 230, and is a device for storing data. The storage device 908 may include a storage medium, a recording device that records data in the storage medium, a reading device that reads data from the storage medium, and a deletion device that deletes data recorded in the storage medium. The storage device 908 drives a hard disk, and stores a program to be executed by the CPU 901 and various types of data.

The drive 909 is a reader/writer for a storage medium, and is built in or attached externally to the image processing apparatus 230. The drive 909 reads information recorded in a removable recording medium such as a magnetic disk, an optical disk, a magneto-optical disk, or a semiconductor memory inserted in the drive 909, and outputs the information to the RAM 903.

The connection port 911 is an interface for connection with an external device, and is a port for connection with an external device capable of data transmission by, for example, a universal serial bus (USB). Furthermore, the communication device 913 is, for example, a communication interface constituted by a communication device or the like for connection to a communication network 5. Furthermore, the communication device 913 may be a wireless local area network (LAN) compatible communication device, a wireless USB compatible communication device, or a wired communication device that performs a wired communication.

The preferred embodiment of the present disclosure has been described above in detail with reference to the accompanying drawings, but the technical scope of the present disclosure is not limited to such an example. It is obvious that a person having ordinary knowledge in the technical field of the present disclosure can come up with various changes and modifications within the scope of the technical idea described in the claims, and such various changes and modifications are naturally understood to belong to the technical scope of the present disclosure.

Furthermore, the effects described in the present specification are merely illustrative or exemplary, and are not restrictive. That is, the technology according to the present disclosure can exhibit other effects that are obvious to those skilled in the art from the description in the present specification, in addition to or instead of the above effects.

Note that configurations as described below also belong to the technical scope of the present disclosure.

(1)
An intraocular lens including:
an optical part having a mark that is detectable under illumination of a specific wavelength range outside a wavelength range of visible light; and
a support part that supports the optical part,
in which the mark is indicated by a geometric pattern that allows for identification of an optical center position of the optical part and information regarding posture of the optical part in an eye.

(2)
The intraocular lens according to (1), in which the geometric pattern of the mark is constituted by a dot or a line, and a combination of these components.

(3)
The intraocular lens according to (1) or (2), in which the mark indicates the optical center position of the optical part by a barycentric position of the geometric pattern, a singular point, or a virtual point identified on the basis of a component constituting the geometric pattern.

(4)
The intraocular lens according to any one of (1) to (3), in which the mark indicates a tilt of the intraocular lens, as information regarding posture of the optical part, by a distortion of the geometric pattern, or a misalignment between at least two of the geometric patterns placed at different positions in a direction of an optical axis of the optical part.

(5)
The intraocular lens according to any one of (1) to (4), in which the mark indicates a depth position of the intraocular lens, as information regarding posture of the optical part, by barycentric positions of at least two of the geometric patterns provided at different positions in a direction of an optical axis of the optical part, singular points, or virtual points identified on the basis of components constituting the geometric patterns.

(6)
The intraocular lens according to any one of (1) to (5), in which the mark is applied in such a way that the mark includes at least the optical center position of the optical part.

(7)
The intraocular lens according to any one of (1) to (6), in which the optical part is further provided with a second mark that allows for identification of lens information relating to characteristics or manufacturing of the intraocular lens.

(8)
The intraocular lens according to any one of (1) to (7), in which the mark is applied to the optical part by using a paint constituted by a substance that causes unique absorption or scattering, fluorescence, or polarization in the specific wavelength range.

(9)
An intraocular lens fixing assistance system including:
an illumination device that irradiates an intraocular lens having an optical part having a mark that is detectable under illumination of a specific wavelength range outside a wavelength range of visible light with illumination light in at least the specific wavelength range outside the wavelength range of visible light;
an image pickup device that images the intraocular lens to acquire an image by light in the specific wavelength range;
an image processing apparatus that extracts the mark from the image and identifies an optical center position and posture information of the intraocular lens; and
a control device that displays the optical center position and the posture information of the intraocular lens on a display device.

(10)
An image processing apparatus including
a processing unit that
extracts, from an image acquired by irradiating an intraocular lens having an optical part having a mark that is detectable under illumination of a specific wavelength range outside a wavelength range of visible light with illumination light in at least the specific wavelength range outside the wavelength range of visible light, the mark from the intraocular lens, and
identifies an optical center position and posture information of the intraocular lens.

REFERENCE SIGNS LIST

1 Intraocular lens fixing assistance system
1 Iris
8a Anterior capsule incision circle
10 Eyeball image
11 Mark
13 Arrow mark
15 Label
100 Intraocular lens
110 Optical part
120 Support part
130, 131, 133 Mark
210 Illumination device
220 Infrared image pickup device
221 Visible light image pickup device
223 Infrared image pickup device
230 Image processing apparatus
231 Marking pattern definition information storage unit
233 Intraocular lens information restoration unit
235 Presentation image generation unit
240 Display device
310 Surgical microscope
320 Wide-angle observation system
321 Front-end lens

The invention claimed is:
1. An intraocular lens, comprising:
an optical part that includes:
a front surface and a back surface; and
at least one mark including a first geometric pattern at the front surface and a second geometric pattern at the back surface, wherein the first geometric pattern is same as the second geometric pattern, the first geometric pattern is at an optical center position of the optical part on the front surface, the second geometric pattern is at the optical center position of the optical part on the back surface, and the at least one mark is detectable under illumination of a specific wavelength range outside a wavelength range of visible light; and a support part configured to support the optical part, wherein the at least one mark is for identification of each of the optical center position of the optical part and information regarding posture of the optical part in an eye, the at least one mark indicates the information regarding the posture based on a misalignment between the first geometric pattern on the front surface of the optical part and the second geometric pattern on the back surface of the optical part in a depth direction of the optical part, and the at least one mark indicates an amount of tilt of the intraocular lens and a direction of the tilt based on an amount of displacement between a center position of the first geometric pattern on the front surface of the optical part and a center position of the second geometric pattern on the back surface of the optical part.

2. The intraocular lens according to claim 1, wherein each of the first geometric pattern and the second geometric pattern of the at least one mark includes at least one of a dot or a line.

3. The intraocular lens according to claim 1, wherein the at least one mark indicates the optical center position of the optical part by a barycentric position of one of the first geometric pattern, a singular point, or a virtual point, and each of the singular point and the virtual point is identified based on a component that constitutes the first geometric pattern.

4. The intraocular lens according to claim 1, wherein the at least one mark further indicates the tilt of the intraocular lens, as the information regarding the posture of the optical part, by a distortion of the first geometric pattern.

5. The intraocular lens according to claim 1, wherein the at least one mark indicates a depth position of the intraocular lens based on at least one of:

a plurality of first barycentric positions of a plurality of singular points of the at least one mark, or a plurality of a second barycentric positions of a plurality of virtual points of the at least one mark, and each of the plurality of singular points and the plurality of virtual points is identified based on components that constitute the first geometric pattern.

6. The intraocular lens according to claim 1, wherein the optical part further includes a specific mark different from the at least one mark, the specific mark is for identification of lens information of the intraocular lens, and the lens information is related to at least one of characteristics of the intraocular lens or manufacturing details of the intraocular lens.

7. The intraocular lens according to claim 1, wherein the at least one mark comprises a paint constituted by a substance that causes at least one of absorption, scattering, fluorescence, or polarization in the specific wavelength range.

8. The intraocular lens according to claim 1, wherein in a case where each of the first geometric pattern and the second geometric pattern is in a shape of a circle, and the first geometric pattern is concentric with respect to the second geometric pattern, the amount of the tilt of the intraocular lens is zero.

9. The intraocular lens according to claim 1, wherein the at least one mark indicates a depth position of the intraocular lens based on the misalignment between the first geometric pattern on the front surface of the optical part and the second geometric pattern on the back surface of the optical part.

* * * * *